(12) United States Patent
Nagel et al.

(10) Patent No.: US 9,592,345 B2
(45) Date of Patent: Mar. 14, 2017

(54) ARRANGEMENT AND METHOD FOR DETERMINING A STOPPER POSITION

(71) Applicant: SANOFI-AVENTIS DEUTSCHLAND GMBH, Frankfurt am Main (DE)

(72) Inventors: Thomas Nagel, Tharandt (DE); Rene Richter, Tharandt (DE); Robert Witt, Dresden (DE); Richard Guenther, Dresden (DE); Johannes Vogel, Dresden (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 106 days.

(21) Appl. No.: 14/413,631

(22) PCT Filed: Jul. 10, 2013

(86) PCT No.: PCT/EP2013/064630
§ 371 (c)(1),
(2) Date: Jan. 8, 2015

(87) PCT Pub. No.: WO2014/009442
PCT Pub. Date: Jan. 16, 2014

(65) Prior Publication Data
US 2015/0174330 A1    Jun. 25, 2015

(30) Foreign Application Priority Data

Jul. 11, 2012 (EP) ..................... 12175974

(51) Int. Cl.
*A61M 5/315* (2006.01)
*G01S 15/36* (2006.01)
(Continued)

(52) U.S. Cl.
CPC ............ *A61M 5/315* (2013.01); *G01S 15/36* (2013.01); *G01S 15/88* (2013.01); *A61M 5/1684* (2013.01);
(Continued)

(58) Field of Classification Search
CPC .......... A61M 5/315; A61M 2205/3375; A61M 2205/3389; A61M 5/1684; A61M 5/31568;
(Continued)

(56) References Cited

U.S. PATENT DOCUMENTS

| 4,811,595 A | 3/1989 | Marciniak et al. |
| 4,936,143 A | 6/1990 | Schutten et al. |

(Continued)

FOREIGN PATENT DOCUMENTS

| CN | 101809406 A | 8/2010 |
| CN | 101918058 A | 12/2010 |

(Continued)

OTHER PUBLICATIONS

International Search Report for Int. App. No. PCT/EP2013/064630, completed Jul. 25, 2013.

(Continued)

*Primary Examiner* — Daniel Pihulic
(74) *Attorney, Agent, or Firm* — Fish & Richardson P.C.

(57) ABSTRACT

The invention relates to an arrangement for determining a position (x) of a stopper relative to a container in a drug delivery device, comprising an acoustic source configured to emit an acoustic signal and an acoustic sensor configured to detect an acoustic signal, a processing unit for controlling the acoustic source and processing the detected acoustic signal for determining characteristics of the acoustic signal correlated with the position (x) of the stopper. Furthermore, the invention relates to a method for determining a position (Continued)

(x) of a stopper relative to a container in a drug delivery device, the method comprising the steps of emitting an acoustic signal from an acoustic source, detecting an acoustic signal caused by the emitted acoustic signal by means of an acoustic sensor, and processing the detected acoustic signal for determining characteristics of the acoustic signal correlated with the position (x) of the stopper by means of a processing unit.

12 Claims, 3 Drawing Sheets

(51) Int. Cl.
*G01S 15/88* (2006.01)
*A61M 5/168* (2006.01)

(52) U.S. Cl.
CPC . *A61M 5/31568* (2013.01); *A61M 2205/3306* (2013.01); *A61M 2205/3375* (2013.01); *A61M 2205/3389* (2013.01)

(58) Field of Classification Search
CPC . A61M 2205/3306; G01S 15/36; G01S 15/88
See application file for complete search history.

(56) References Cited

U.S. PATENT DOCUMENTS

| | | | | |
|---|---|---|---|---|
| 4,980,868 A | * | 12/1990 | Teel | G01S 7/526 367/904 |
| 5,241,278 A | | 8/1993 | Bitar | |
| 6,113,578 A | * | 9/2000 | Brown | A61B 5/14532 222/23 |
| 7,679,562 B2 | * | 3/2010 | Shirakawa | G01S 13/003 342/118 |
| 8,333,188 B2 | | 12/2012 | Masada et al. | |
| 2003/0110967 A1 | | 6/2003 | McAnally et al. | |
| 2005/0135190 A1 | * | 6/2005 | Katou | G01S 15/104 367/99 |
| 2010/0288036 A1 | | 11/2010 | Volkwein | |
| 2013/0158711 A1 | * | 6/2013 | Smith | B25J 9/1694 700/259 |
| 2014/0207080 A1 | * | 7/2014 | Allerdings | A61M 5/168 604/207 |
| 2015/0174330 A1 | * | 6/2015 | Nagel | A61M 5/315 604/218 |

FOREIGN PATENT DOCUMENTS

| | | | | |
|---|---|---|---|---|
| CN | 104428688 A | * | 3/2015 | A61M 5/315 |
| DE | 102006047537 | | 4/2008 | |
| DE | WO 2014009442 A1 | * | 1/2014 | A61M 5/315 |
| DE | EP 2872917 A1 | * | 5/2015 | A61M 5/315 |
| EP | 0395008 A1 | | 10/1990 | |
| EP | 1726261 | | 11/2006 | |
| JP | H07-083727 | | 3/1995 | |
| WO | 03053695 A1 | | 7/2003 | |
| WO | 2009/015741 | | 2/2009 | |
| WO | 2011/032960 | | 3/2011 | |
| WO | 2011032960 A1 | | 3/2011 | |
| WO | 2012/038686 | | 3/2012 | |
| WO | 2012038686 A1 | | 3/2012 | |
| WO | 2013/034716 | | 3/2013 | |

OTHER PUBLICATIONS

English Translation of First Office Action issued in Chinese Patent Application No. 201380036504.2 dated May 30, 2016.
Extended European Search Report in European Application No. 16180037.0, dated Dec. 5, 2016, 7 pages.

* cited by examiner

ARRANGEMENT AND METHOD FOR DETERMINING A STOPPER POSITION

CROSS REFERENCE TO RELATED APPLICATIONS

The present application is a U.S. National Phase Application pursuant to 35 U.S.C. §371 of International Application No. PCT/EP2013/064630 filed Jul. 10, 2013, which claims priority to European Patent Application No. 12175974.0 filed Jul. 11, 2012. The entire disclosure contents of these applications are herewith incorporated by reference into the present application.

TECHNICAL FIELD

The invention relates to an arrangement and a method for determining a stopper position within a container of a drug delivery device.

BACKGROUND

Drug delivery devices such as syringes or ampoules usually comprise a hollow cylinder made of a pharmaceutical glass which is inert and chemically resistant against the drug stored inside, e.g. insulin. The container is sealed by a stopper or bung at one end of the cylinder which can be moved along the longitudinal axis of the cylinder in order to displace the drug and force it out of an outlet end which may be sealed by a piercable membrane. The stopper and the piercable membrane are conventionally made of an elastomere ensuring mechanical tightness under defined pressure conditions and long term germ impermeability.

When automatically dosing drugs, it may be desirable to detect the amount of drug in the container, e.g. by detecting the position of the stopper in the container. Hence a remaining quantity of the drug in the container can be calculated for a given geometry of the medicament container and a given longitudinal position of the stopper. This allows for an automatic dosing of the medicament, e.g. in an electromechanical insulin pen.

SUMMARY

It is an object of the present invention to provide an improved arrangement and an improved method for determining a stopper position within a container of a drug delivery device.

The object is achieved by an arrangement according to claim 1 and by a method according to claim 11.

Preferred embodiments of the invention are given in the dependent claims.

According to the invention, an arrangement for determining a position of a stopper relative to a container in a drug delivery device comprises an acoustic source configured to emit an acoustic signal and an acoustic sensor configured to detect an acoustic signal, a processing unit for controlling the acoustic signal source and processing the detected acoustic signal for determining characteristics of the acoustic signal correlated with the position of the stopper.

According to the invention a method for determining a position of a stopper relative to a container in a drug delivery device comprises the steps of:

emitting an acoustic signal from an acoustic source,
detecting an acoustic signal caused by the emitted acoustic signal by means of an acoustic sensor,
processing the detected acoustic signal for determining characteristics of the acoustic signal correlated with the position of the stopper by means of a processing unit.

In one embodiment of the invention the acoustic source is aligned to emit the acoustic signal through a proximal opening of the container towards the stopper, wherein the processing unit is configured to control the acoustic source so as to emit a coded, e.g. pulsed or modulated acoustic wave and to determine a delay or phase shift of the detected acoustic wave related to the position.

The measurement method is based on the determination of acoustic waves propagating in a medium, e.g. air. With this method distances may be determined by measuring delays or phase shifts. Acoustical measurement methods are affected by temperature and air humidity as these influencing quantities affect the sonic velocity. Therefore, the arrangement and the method may be improved by providing respective sensors for acquiring temperature and air humidity and taking these parameters into account when calculating the distances.

The acoustic wave may be an ultrasonic wave, which is non-audible to humans so as to avoid confusing a user. The acoustic wave may likewise be in the audible frequency band.

The acoustic source and the acoustic sensor may be arranged separately or be integrated in a sound converter operatively switchable to act as either the acoustic source or the acoustic sensor.

In another embodiment the acoustic source may be aligned to emit the acoustic signal into a resonance volume, which is defined in one spatial dimension by the position of the stopper, wherein the processing unit is configured to vary the frequency of the emitted acoustic signal within a predetermined frequency range, wherein the processing unit is configured to detect a harmonic of a resonance frequency characteristic for the resonance volume related to the position.

The resonance volume forms an oscillatory system with a resonance frequency which is characteristic for the size and geometry of the resonance volume according to the laws of Kundt's tube. If Kundt's tube is excited with the resonance frequency a standing wave forms, such that an amplitude of the resonance frequency increases and can be measured by the acoustic sensor, e.g. a microphone.

The measuring method determines the distance by measuring resonances caused by acoustic waves in the resonance volume. Acoustical measurement methods are affected by temperature and air humidity as these influencing quantities affect the sonic velocity. Therefore, the arrangement and the method may be improved by providing respective sensors for acquiring temperature and air humidity and taking these parameters into account when calculating the distances.

The resonance volume may at least partially be defined within a proximal end of the container.

Typically, the stopper of an unused container may be positioned at the very proximal end or just a very short distance within the container so that no resonance volume at all or just a very small resonance volume is provided. This would result in a very high resonance frequency, which may be out of the range of the acoustic source and/or the acoustic sensor. In order to allow for employing the resonance measuring method even if the stopper were positioned at the very proximal end of the container, a tube section with essentially or exactly the same internal diameter as the container is arranged proximally adjacent the container, so that a resonance volume exists regardless of the position of the stopper.

The pre-determined frequency range may be selected so as to match at least part of a range of linear frequency response of the acoustic source.

In an exemplary embodiment the acoustic source may be controlled to emit acoustic waves in a frequency range from 0 to 10 kHz. However, other frequency ranges in the audible or non-audible range may be selected.

If the acoustic source has a non-linear frequency response in the pre-determined frequency range the acoustic source and acoustic sensor may be intensity calibrated at least for the pre-determined frequency range so as to compensate the non-linearities.

The arrangement for determining the position of the stopper relative to the container may be applied in a drug delivery device with a container defining a cavity for a drug and a stopper for proximally delimiting the cavity and displacing the drug from the cavity.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
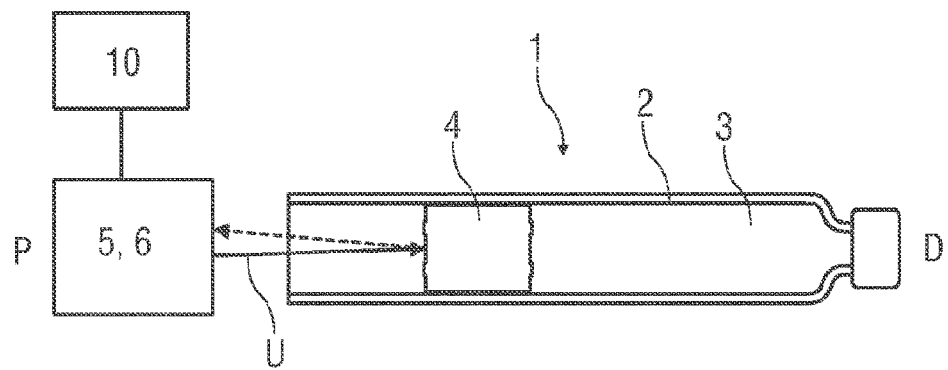
FIG. 1 is a schematic longitudinal section of a drug delivery device with an ultrasonic transmitter-sensor-arrangement for determining a stopper position.

FIG. 1 is a schematic longitudinal section of a drug delivery device 1. The drug delivery device 1 comprises a cylindrical container 2 defining a cavity 3 for a drug. The cavity 3 is proximally delimited by a stopper 4 which may be translated within the container 2 for displacing the drug from the cavity 3 through a discharge nozzle (not illustrated) arrangeable at a distal end of the container 2. An acoustic source 5 and an acoustic sensor 6 designed as an ultrasonic transmitter-sensor-arrangement are arranged for determining a position of the stopper 4 relative to the container 2 by measuring the distance between the ultrasonic transmitter-sensor-arrangement 5, 6 and the stopper 4. The ultrasonic transmitter-sensor-arrangement 5, 6 should therefore be fixed in position relative to the container 2. The ultrasonic transmitter-sensor-arrangement 5, 6 is operated with a frequency which is non-audible for a human, e.g. in the range between 20 kHz and 400 kHz. The ultrasonic transmitter-sensor-arrangement 5, 6 comprises an acoustic source 5, also referred to as a transmitter and an acoustic sensor 6, also referred to as a receiver. In an exemplary embodiment the ultrasonic transmitter-sensor-arrangement 5, 6 is arranged as a sound converter for minimizing the foot print. The sound converter may be operated as an acoustic source 5 for emitting a coded, e.g. pulsed or modulated ultrasonic wave U and switched to operate as an acoustic sensor 6 after lapse of a pre-determined time window. Within this time window the coded ultrasonic wave U hits the device under test, i.e. the stopper 4, which reflects the ultrasonic wave U so that it can be detected by the acoustic sensor 6. The processing unit 10 then determines the delay or phase shift of the detected ultrasonic wave with respect to the emitted ultrasonic wave U. The time window and the sonic velocity determine a minimum distance, which has to be adjusted between the ultrasonic transmitter-sensor-arrangement 5, 6 and the stopper 4. For an exemplary measuring frequency of 400 kHz the minimum distance would be approximately 20 mm.

Controlling the acoustic source 5 and acoustic sensor 6 as well as coding the ultrasonic wave U, processing the detected ultrasonic wave and determining the distance may be performed by a processing unit 10, which may likewise be integrated in the ultrasonic transmitter-sensor-arrangement 5, 6.

Figure 2:
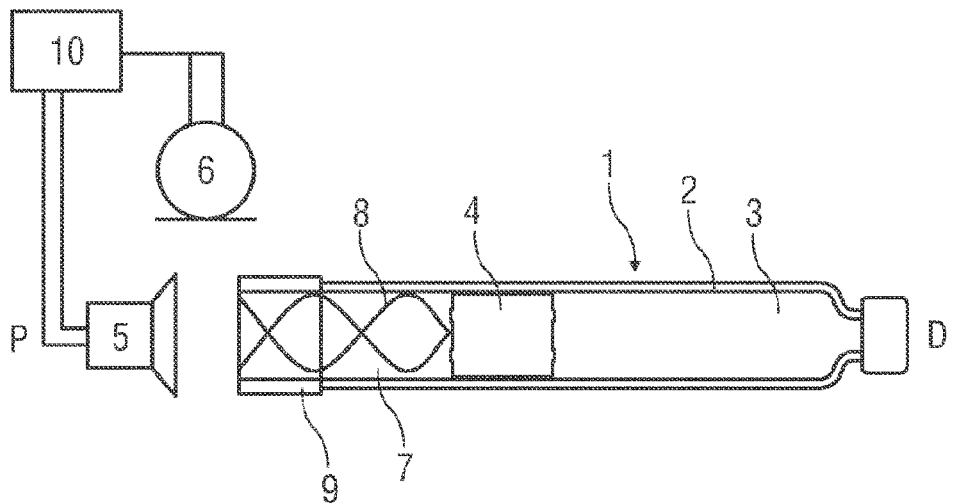
FIG. 2 is a schematic longitudinal section of a drug delivery device with a acoustic source and a acoustic sensor for a resonance based determination of a stopper position.

FIG. 2 is a schematic longitudinal section of a drug delivery device 1 with an acoustic source 5 and an acoustic sensor 6 for a resonance based determination of a position of the stopper 4. The drug delivery device 1 comprises a cylindrical container 2 defining a cavity 3 for a drug. The cavity 3 is proximally delimited by a stopper 4 which may be translated within the container 2 for displacing the drug from the cavity 3 through a discharge nozzle (not illustrated) arrangeable at a distal end of the container 2. An acoustic source 5 and an acoustic sensor 6 are arranged for determining a position of the stopper 4.

The stopper 4 in FIG. 2 is shown at a position within the container 2 so that a resonance volume 7 filled with air is defined proximally from the stopper 4 within the container 2. The position of the stopper 4 may be determined by measuring resonances caused by acoustic waves within this resonance volume 7. The resonance volume 7 forms an oscillatory system with a resonance frequency which is characteristic for the size and geometry of the resonance volume 7 according to the laws of Kundt's tube. If Kundt's tube is excited with the resonance frequency a standing wave 8 forms, such that an amplitude of the resonance frequency increases and can be measured by the acoustic sensor 6, e.g. a microphone.

Figure 3:
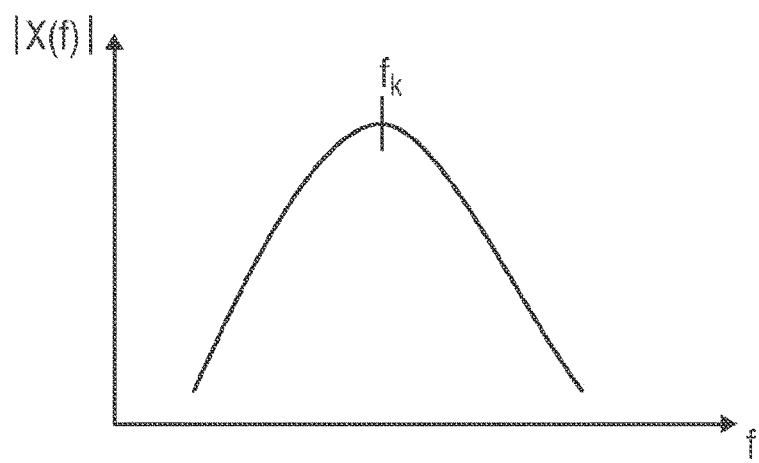
FIG. 3 is a diagram showing an amplitude of the acoustic signal detected by the acoustic sensor depending on the frequency of the acoustic signal.

The acoustic source 5 may be controlled by a processing unit 10 to wobble through a defined frequency band, i.e. to emit sound waves with frequencies varying within this frequency band. The sound waves acquired by the acoustic sensor 6 may be analyzed in the processing unit 10 for determining the maximum amplitude and thus the resonance frequency. FIG. 3 is a diagram showing a typical amplitude spectrum |X(f)| of the acoustic signal detected by the acoustic sensor 6 depending on the frequency f of the acoustic signal emitted by the acoustic source 5 into the resonance volume 7. The amplitude |X(f)| has a maximum at the resonance frequency $f_k$. The position of the stopper 4 can then be determined by equation (1):

$$f_k = (2k-1) \cdot \frac{c}{4l}, k \in N, \qquad (1)$$

wherein c is the sonic velocity in air, l is the length of the cylindrical resonance volume 7 and k is the harmonic index.

Typically, the stopper 4 of an unused container 2 is positioned at the very proximal end or just a very short distance within the container 2 so that no resonance volume 7 at all or just a very small resonance volume 7 is provided. This would result in a very high resonance frequency $f_k$, which may be out of the range of the acoustic source 5 and/or the acoustic sensor 6. In order to allow for employing the resonance measuring method even with the stopper 4 positioned at the very proximal end of the container 2, a tube section 9 with essentially or exactly the same internal diameter as the container 2 is arranged proximally adjacent the container 2, so that a resonance volume 7 exists regardless the position of the stopper 4 (cf. FIG. 2). In an exemplary embodiment the tube section 9 has a length of 10 mm.

Figure 4:
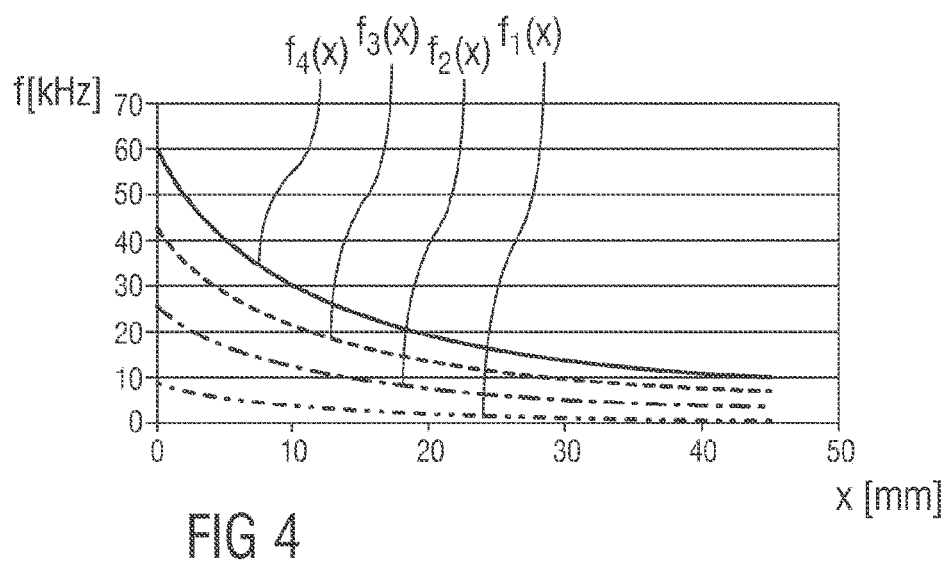
FIG. 4 is a diagram showing a resonance frequency depending on the stopper position.

FIG. 4 is a diagram showing the resonance frequency $f_K$ depending on the position x of the stopper 4 relative to the proximal end of the container 2. FIG. 4 illustrates the fundamental resonance frequency or first harmonic $f_1(x)$ with k=1, the second harmonic $f_2(x)$ with k=2, the third harmonic $f_3(x)$ with k=3 and the fourth harmonic $f_4(x)$ with k=4.

Figure 5:
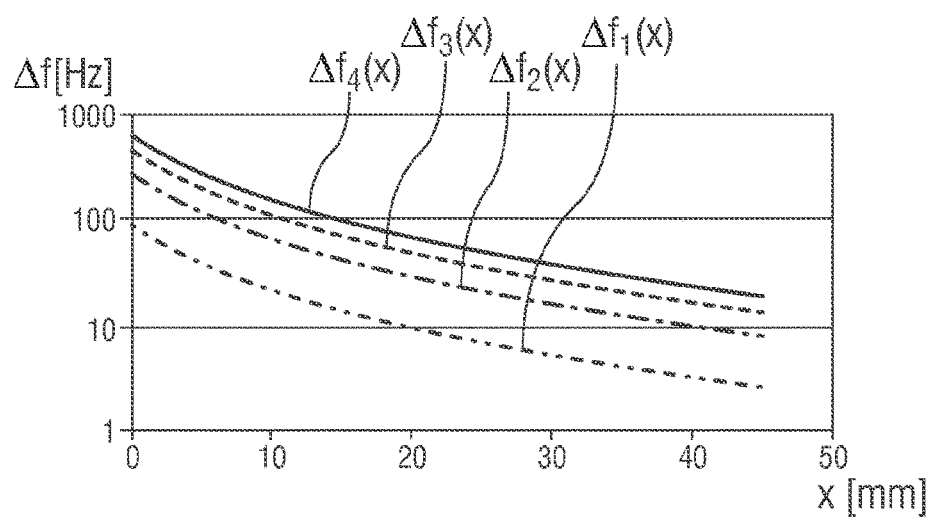
FIG. 5 is a diagram showing a frequency shift of the resonance frequency depending on the stopper position.

FIG. 5 is a diagram showing a frequency shift $\Delta f$ of the resonance frequency $f_k$ depending on the position x of the stopper 4 when varying the position x by 0.1 mm.

As can be seen in FIG. 5 the change of the resonance frequency $\Delta f_1(x), \Delta f_2(x), \Delta f_3(x), \Delta f_4(x)$ for the first, second, third and fourth harmonic $f_1(x), f_2(x), f_3(x), f_4(x)$ between two positions x of the stopper 4 at small distances or positions x of the stopper 4 from the proximal end of the container 2, e.g. x=5 mm, is relatively high. However, according to equation (1) the amount of change $\Delta f_1(x), \Delta f_2(x), \Delta f_3(x), \Delta f_4(x)$ decreases with higher distances or positions x of the stopper 4.

In an exemplary embodiment the method for determining the position x of the stopper 4 is performed with the fundamental frequency $f_1(x)$. The acoustic source 5 emits acoustic waves in the frequency range from 0 to 10 kHz. In order to achieve a uniform intensity, the acoustic source 5 should have a linear frequency response at least within the intended frequency band. The acoustic sensor 6 acquires the power amplitude of the sound in the resonance volume 7, which is stored and assigned to the respective frequency f by the processing unit 10. If the generated frequency matches the resonance frequency $f_1(x)$, resonance occurs resulting in an increased power signal detected by the acoustic sensor 6 (cf. FIG. 3).

The aforementioned arrangements and methods may be applied for measuring fill levels in containers such as glass ampoules for dosing liquids, e.g. drugs.

The aforementioned arrangements and methods allow for reducing the required space and part count and to improve handling.

The invention claimed is:

1. A drug delivery device with a container defining a cavity for a drug and a stopper for proximally delimiting the cavity and displacing the drug from the cavity, the drug delivery device further comprising an arrangement for determining a position (x) of the stopper relative to the container, the arrangement comprising an acoustic source configured to emit an acoustic signal and an acoustic sensor configured to detect an acoustic signal, a processing unit for controlling the acoustic source and processing the detected acoustic signal for determining characteristics of the acoustic signal correlated with the position (x) of the stopper, wherein the acoustic source is aligned to emit the acoustic signal into a resonance volume, which is defined in one spatial dimension by the position of the stopper, wherein the processing unit is configured to vary the frequency (f) of the emitted acoustic signal within a pre-determined frequency range, wherein the processing unit is configured to detect a harmonic ($f_1(x)$, $f_2(x)$, $f_3(x)$, $f_4(x)$) of a resonance frequency $f_k$ characteristic for the resonance volume related to the position (x).

2. The drug delivery device according to claim 1, wherein the acoustic source is aligned to emit the acoustic signal through a proximal opening of the container towards the stopper, wherein the processing unit is configured to control the acoustic source so as to emit a coded acoustic wave (U) and to determine a delay or phase shift of the detected acoustic wave related to the position (x).

3. The drug delivery device according to claim 2, wherein the acoustic wave (U) is an ultrasonic wave (U).

4. The drug delivery device according to claim 2, wherein the acoustic source and the acoustic sensor are integrated in a sound converter operatively switchable to act as either the acoustic source or the acoustic sensor.

5. The drug delivery device according to claim 1, wherein the resonance volume is at least partially defined within a proximal end of the container.

6. The drug delivery device according to claim 1, wherein a tube section with essentially the same internal diameter as the container is arranged proximally adjacent the container for at least partially defining the resonance volume.

7. The drug delivery device according to claim 1, wherein the pre-determined frequency range is selected so as to match at least part of a range of linear frequency response of the acoustic source.

8. A method for determining a position (x) of a stopper relative to a container in a drug delivery device, the method comprising the steps of:
aligning an acoustic source to emit an acoustic signal into a resonance volume, which is defined in one spatial dimension by the position of the stopper;
emitting the acoustic signal from an acoustic source, wherein the frequency (f) of the emitted acoustic signal is varied within a pre-determined frequency range;
detecting, by an acoustic sensor, an acoustic signal caused by the emitted acoustic signal, wherein a harmonic ($f_1(x)$, $f_2(x)$, $f_3(x)$, $f_4(x)$) of a resonance frequency $f_k$ characteristic for the resonance volume related to the position (x) is detected; and
processing the detected acoustic signal for determining characteristics of the acoustic signal correlated with the position (x) of the stopper by means of a processing unit.

9. The method according to claim 8, wherein the acoustic source is aligned to emit the acoustic signal through a proximal opening of the container towards the stopper, wherein the acoustic source is controlled so as to emit a coded acoustic wave (U) and wherein a delay or phase shift of the detected acoustic wave related to the position (x) is determined.

10. The method according to claim 9, wherein the acoustic wave (U) is an ultrasonic wave (U).

11. The method according to claim 9, wherein the acoustic source and the acoustic sensor are integrated in a sound converter which is operatively switched to act as either the acoustic source or the acoustic sensor.

12. The method according to claim 8, wherein the pre-determined frequency range is selected so as to match at least part of a range of linear frequency response of the acoustic source.

* * * * *